Figure 1:
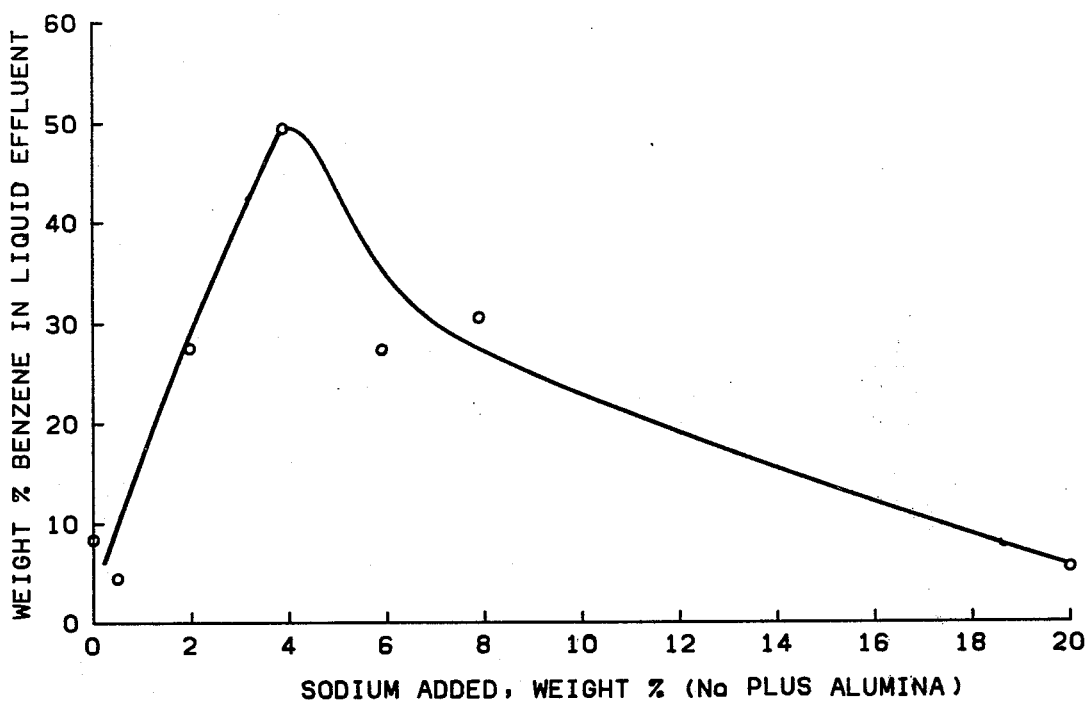

| United States Patent [19] | [11] | 4,151,071 |
|---|---|---|
| Myers | [45] | Apr. 24, 1979 |

[54] DEHYDROCYCLIZATION PROCESS

[75] Inventor: John W. Myers, Bartlesville, Okla.

[73] Assignee: Phillips Petroleum Company, Bartlesville, Okla.

[21] Appl. No.: 819,028

[22] Filed: Jul. 26, 1977

[51] Int. Cl.$^2$ .................. C07C 15/02; B01J 23/04; B01J 23/26

[52] U.S. Cl. .................. 208/135; 208/136; 252/463; 260/668 D; 260/673.5

[58] Field of Search .................. 260/673.5, 668 D; 252/463, 465; 208/135, 136

[56] References Cited

U.S. PATENT DOCUMENTS

| 2,857,442 | 10/1958 | Hay | 260/673.5 |
|---|---|---|---|
| 2,972,644 | 2/1961 | Holmes et al. | 260/673.5 |
| 3,240,832 | 3/1966 | Ryan | 260/673.5 |
| 3,285,985 | 11/1966 | Kline et al. | 260/673.5 |
| 3,428,702 | 2/1969 | Downs et al. | 260/673.5 |
| 3,501,542 | 3/1970 | Carr et al. | 260/673.5 |
| 3,836,603 | 9/1974 | Connor et al. | 260/673.5 |
| 3,890,218 | 6/1975 | Morrison | 208/135 |
| 3,925,254 | 12/1975 | Oishi | 252/455 Z |

*Primary Examiner*—Delbert E. Gantz
*Assistant Examiner*—G. E. Schmitkons

[57] ABSTRACT

Nonaromatic hydrocarbons are converted to aromatic hydrocarbons by contacting with a catalyst of alumina promoted with an alkali metal oxide and, optionally, chromium oxide under dehydrocyclization conditions of temperature and pressure. In a specific embodiment, hexene-1 and heptene-1 are converted, respectively, to benzene and toluene in the presence of alkali metal oxide-alumina catalysts, optionally promoted with chromium oxide, with good conversion and high selectivity.

9 Claims, 2 Drawing Figures

DEHYDROCYCLIZATION PROCESS

This invention relates to reforming hydrocarbons. In accordance with another aspect, this invention relates to the dehydrocyclization of nonaromatic hydrocarbons in the presence of a catalyst which is alumina promoted with an alkali metal oxide and, optionally, chromium oxide. In accordance with a further aspect, this invention relates to the forming of naphthas from nonaromatic hydrocarbons by contacting with a catalyst consisting essentially of alumina promoted with an oxide of sodium, potassium, rubidium, or cesium. In accordance with a further aspect, this invention relates to the dehydrocyclization of nonaromatic hydrocarbons in the presence of a catalyst such as alumina promoted with an oxide of sodium or potassium and chromium oxide.

It is well known that aliphatic hydrocarbons, both saturated and unsaturated, can be converted through dehydrocyclization into aromatic hydrocarbons. The aromatic hydrocarbons are valuable organic chemicals and have particular value for motor fuels in providing high antiknock ratings. Usually the antiknock ratings of aromatic hydrocarbons are substantially higher than those of aliphatic hydrocarbons, particularly those aliphatic hydrocarbons having six or more carbon atoms in a linear chain found in natural gasoline and intermediate and higher boiling fractions such as straight run gasoline and naphtha streams separated from crude petroleum in refining operations. The present invention is directed to a process for converting aliphatic hydrocarbons to aromatic hydrocarbons. The instant process gives good yields and offers industry an efficient and economical method to produce aromatic hydrocarbons.

Accordingly, an object of this invention is to provide an improved hydrocarbon conversion process whereby the yield of converted hydrocarbon is increased.

A further object of this invention is to provide an improved process for the reforming of aliphatic hydrocarbons.

Another object of this invention is to provide a catalyst which is active for the dehydrocyclization of nonaromatic hydrocarbons.

Other objects, aspects, and the several advantages of the invention will be apparent to those skilled in the art upon reading the specification and the appended claims.

In accordance with the invention, nonaromatic hydrocarbons are dehydrocyclized to aromatic hydrocarbons by contacting nonaromatic hydrocarbon-containing feeds with a catalyst consisting essentially of alumina promoted with an alkali metal oxide and, optionally, chromium oxide under dehydrocyclization conditions of temperature and pressure.

In accordance with a specific embodiment, hexene-1 is converted to benzene by contacting with a catalyst consisting essentially of alumina promoted with an oxide of sodium, potassium, rubidium, or cesium under dehydrocyclization conditions.

In accordance with a further specific embodiment, hexene-1 and heptene-1 are converted, respectively, to benzene and toluene by contacting with a catalyst consisting essentially of alumina promoted with an oxide of sodium or potassium and chromium oxide under dehydrocyclization conditions.

The catalysts employed in the present invention are particularly applicable to the dehydrocyclization and reforming of aliphatic hydrocarbons including acyclic and cyclic hydrocarbons. Suitable hydrocarbon feedstocks which can be used include olefinic hydrocarbons and paraffin hydrocarbons containing from six to about twelve carbon atoms per molecule, each compound characterized by having at least six carbon atoms in a straight chain. Feedstocks comprising monoolefins are presently preferred. Representative examples of suitable monoolefins that can be dehydrocyclized according to the invention include hexene, heptene, octene, decene, dodecene, including mixtures thereof, and the like. Naphthenes containing from six to about twelve carbon atoms per molecule are also suitable feedstocks providing each naphthene has six or more carbon atoms in the naphthene ring. Mixtures of hydrocarbons in the feedstock can be employed.

In addition, mixtures of hydrocarbons boiling in the gasoline range, e.g., 100°–425° F. (38°–218° C.), which are relatively free of aromatic hydrocarbons, can be upgraded in aromatic content by utilizing the catalysts of this invention in a dehydrocyclization process. Cat cracker gasoline or other gasoline fractions, for example, can be upgraded as a motor fuel by increasing aromatic content in this fashion.

The catalyst of the invention consists essentially of alumina having a surface area of at least 50 $m^2/g$ and a suitable alkali metal oxide promoter selected from among sodium, potassium, rubidium, and cesium. Sodium and potassium are presently preferred because of ready availability and low cost. Alumina normally used as catalyst supports and an alkali metal compound which is convertible to the oxide at subsequent calcination are mixed to produce the alumina-alkali metal oxide catalysts of this invention. Suitable alkali metal compounds, for example, are selected from among the oxides, hydroxides, bicarbonates, carbonates, and salts of weak acids, e.g., acetates, formates, etc., and the like. The salts of strong acids, e.g., halides, are unsuitable for this purpose. However, the sulfates are fairly satisfactory with the chromia-containing catalysts. Silica cannot be substituted for alumina in the catalyst systems since low activity for dehydrocyclization results.

As indicated above, the alkali metal oxide-alumina catalysts of the invention can optionally contain an oxide of chromium as a second promoter. Chromium oxide is generally used only with an oxide of sodium or potassium on alumina. Thus, the metal promoter can be added in oxide form or as a compound convertible to an oxide at subsequent calcination conditions. Suitable compounds, for example, include chromium trioxide, chromium acetate, chromium nitrate, sodium chromate, and potassium dichromate.

The catalysts of this invention can be prepared by dry blending, by impregnation of alumina or alumina-chromia with one or more solutions of the appropriate metal compound or compounds and the like. The resulting mixture is dried, if necessary, and calcined in air at about 700°–1200° F. (371°–650° C.) for from about one to 20 hours. The resulting product can be ground and sized, converted to pellets, etc., using conventional pelleting practices.

The concentration of metal oxide promoters in the catalysts, in terms of weight percent, is related to the surface area of the alumina and the particular alkali metal oxide chosen. For convenience, however, the promoter concentration is expressed as weight percent of the support plus added metal ion or ions. The weight ratio of alkali metal/chromium is dependent upon the alkali metal selected. Although the metal promoters are in the form of their oxides after calcination of catalyst;

for convenience, the concentrations shown are calculated as the metal. The following tables disclose operable ranges for the catalysts.

TABLE A

| Alkali Metal Oxide/Alumina Catalysts | | |
|---|---|---|
| Alumina Surface Area, m$^2$/g | Na or K (Wt. Percent) | Rb or Cs (Wt. Percent) |
| 50–150 | 2–8 | 3–12 |
| 150–350 (or higher) | 5–14 | 6–18 |

TABLE B

| Alkali Metal Oxide/Chromia/Alumina Catalysts | | | | | | | |
|---|---|---|---|---|---|---|---|
| Alumina Surface Area m$^2$/g | Na Wt. % | Cr Wt. % | Na/Cr (Wt. Ratio) Broad | Preferred | K Wt. % | Cr Wt. % | K/Cr (Wt. Ratio) Broad | Preferred |
| 50–150 | 3–12 | 1.4–24 | 0.5–2.2 | 0.6–2.0 | 5–16 | 3.3–22.9 | 0.7–1.5 | 0.8–1.3 |
| 150–350 | 6–18 | 3.3–15 | 1.2–1.8 | 1.3–1.7 | 8–20 | 5.3–28.6 | 0.7–1.5 | 0.8–1.3 |

When compositions falling within the above ranges are used, active dehydrocyclization catalysts result which, however, possess relatively low activity for hydrogenation under the reaction conditions employed. By low hydrogenation activity is meant that with hexene-1 or heptene-1 feeds, for example, the liquid effluent containing the olefinic starting hydrocarbon and its paraffinic counterpart contains less than about 28 weight percent of the paraffin and more preferably from about 25 to about 2 weight percent, or even less.

In utilizing the catalysts of this invention for the dehydrocyclization and reforming of the foregoing hydrocarbons, the hydrocarbons to be reformed are contacted under dehydrocyclization conditions with the catalysts of the invention at a temperature, pressure, and flow rate of feedstock sufficient to convert the nonaromatic hydrocarbons present in the feedstock to the desired reformed product. Conditions employed will vary appreciably, depending upon feedstock and other conditions.

The dehydrocyclization can be carried out by passing the feed over the catalyst at a temperature ranging from about 700°–1100° F. (371°–593° C.), preferably 800°–1050° F. (427°–565° C.), and a pressure ranging from about 0 to 300 psig (0–2068 kPa gage), preferably 0 to 50 psig (0–345 kPa gage). A low effective pressure of feed can be attained by addition of diluents, e.g., hydrogen, to the reactant stream. A hydrogen/hydrocarbon mole ratio of about 0–5 can be employed in the reaction. The hydrocarbon stock is passed through the reactor at a liquid hourly space velocity (LHSV) ranging from 0.2–5 volumes of hydrocarbon feed per volume of catalyst per hour and preferably in the range of 0.3–2.5 LHSV.

The temperature to be employed in the reforming process will be determined largely by the other operating conditions, that is, at a particular pressure liquid hourly space velocity, the temperature is normally determined by the desired octane number of the product to be produced.

In utilizing the catalyst of this invention for dehydrocyclizing hydrocarbon feedstock, the mode of contact employed can be by fixed or fluidized catalyst bed. The reaction can be carried out continuously or batchwise. In either case, the effluent is separated into components by conventional means such as fractionation, adsorption, solvent extraction, and the like. Unconverted feed can be recycled.

EXAMPLE I

A series of catalysts was prepared by impregnating individual samples of 20–40 mesh particles (U.S. Sieve Series) of a commercially available alumina having a surface area of about 91 m$^2$/g with an aqueous solution of an alkali metal compound. Each composite was dried at about 240° F. (116° C.) and calcined in air for two hours at about 900° F. (482° C.). Each catalyst was charged to a tubular fixed bed reactor and tested for dehydrocyclization of hexene-1 at a pressure of one atmosphere (absolute). Each effluent was cooled in a wet ice bath. The reaction conditions employed and amount of benzene produced, based on liquid effluents, are given in Table I. Total product composition as ascertained by gas-liquid chromatography (GLC) for a typical run is given in Table IA. The Centigrade temperatures given are rounded off to the nearest whole degree. The amount of n-hexane in the n-hexane plus hexene-1 portion of the liquid effluent collected for each run was estimated by subtracting the thermodynamic equilibrium concentration of hexene-1 from the total hexene-1 plus n-hexene determined by GLC. Detailed analyses of other similar products from the runs as exemplified by Table IA show this estimation to be satisfactory.

The benzene yields based on liquid effluents obtained in Runs 1–7 are also presented in graphical form in FIG. 1.

TABLE I

| Dehydrocylization of Hexene-1 over Alkali Metal Oxide/Alumina Catalysts | | | | | | | | | |
|---|---|---|---|---|---|---|---|---|---|
| | | | Test Conditions | | | | Weight Percent | | |
| Run No. | Alkali Metal | (Wt. %) | Compound Used | ° F. | ° C. | LHSV | Sample Period, Hrs.[1] | Benzene | n-Hexane | Remarks |
| 1 | — | 0 | — | 1007 | 542 | 0.5 | 0.7–1.2 | 8.8 | — | Control |
| 2 | Na | 0.5 | NaOH | 1012 | 544 | 0.4 | 1.2–1.7 | 4.5 | — | control |
| 3 | Na | 2.0 | NaOH | 1011 | 544 | 0.5 | 1.2–1.7 | 28.2 | 6 | Invention |
| 4 | Na | 3.9 | NaOH | 1009 | 543 | 0.4 | 1.2–1.7 | 49.9 | 6 | Invention |
| 5 | Na | 5.9 | NaOH | 1001 | 538 | 0.5 | 0.7–1.3 | 27.6 | 6 | Invention |
| 6 | Na | 7.9 | NaOH | 1001 | 538 | 0.5 | 0.9–1.6 | 30.4 | 9 | Invention |
| 7 | Na | 20.0 | NaOH | 1003 | 539 | 0.5 | 0.7–1.0 | 5.9 | — | Control |
| 8 | Li | 4.0 | LiOH | 105 | 541 | 0.6 | 0.7–1.0 | 2.4 | — | Control |
| 9 | K | 3.5 | KOH | 1001 | 538 | 0.45 | 0.7–1.0 | 55.6 | 4 | Invention |
| 10 | K | 6.6 | KOH | 1004 | 540 | 0.45 | 0.7–1.0 | 51.2 | 3 | Invention |
| 11 | Rb | 4.0 | RbOH | 1004 | 540 | 0.6 | 0.7–1.0 | 32.3 | — | Invention |

TABLE I-continued

Dehydrocylization of Hexene-1 over Alkali Metal Oxide/Alumina Catalysts

| Run No. | Alkali Metal (Wt. %)-Compound Used | | | Test Conditions | | | | Weight Percent | | Remarks |
|---|---|---|---|---|---|---|---|---|---|---|
| | | | | °F. | °C. | LHSV | Sample Period, Hrs.[1] | Benzene | n-Hexane | |
| 12 | Rb | 8.0 | RbOH | 1002 | 539 | 0.6 | 0.7–1.0 | 64.3 | — | Invention |
| 13 | Na | 4.0 | Na$_2$SO$_4$ | 1006 | 541 | 0.45 | 0.7–1.3 | 0.3 | — | Control |
| 14 | Na | 4.0 | NaCl | 1009 | 543 | 0.6 | 0.7–1.0 | none detected | — | Control |

[1] Hexene-1 was passed over the catalysts for 0.7–1.2 hrs. (as indicated by the start of the sample period) at about 800–900° F. before these samples were taken.

TABLE IA

Total Product Composition of Run 5 of Table I

| Component | Weight Percent |
|---|---|
| Hydrogen | 2.5 |
| Metane | 5.2 |
| Ethane | 4.5 |
| Ethylene | 2.0 |
| Propane | 0.9 |
| Propylene | 2.7 |
| Butanes | 0.4 |
| Butenes | 7.2 |
| Pentanes | 0.7 |
| C$_5$ monoolefins | 9.6 |
| C$_5$ diolefins | 4.4 |
| Cyclopentene | 0.2 |
| Isohexenes | 0.7 |
| n-Hexenes | 24.9 |
| Hexadienes | 3.5 |
| n-Hexane | 1.5 |
| Methylcyclopentane | 1.0 |
| Benzene | 23.1 |
| Toluene | 2.4 |
| Heptenes | 0.6 |
| C$_8$+ (mostly aromatics) | 2.0 |

Inspection of the results presented in Table I, Run 8, shows that lithium oxide-promoted alumina does not yield an active catalyst. In contrast, Runs 1–7 demonstrate that sodium oxide-promoted alumina, the alumina having a surface area of 91 m$^2$/g, forms active catalyst when the sodium content ranges between about two weight percent and greater than about eight weight percent but less than about 20 weight percent. It is believed that about twelve weight percent sodium constitutes a reasonable upper limit with the alumina used. Runs 9–12 show that potassium- or rubidium-promoted alumina catalysts are active for dehydrocyclization. Comparing results of Runs 4, 9, and 11, it is seen that at roughly equivalent weights of alkali metal, (about four weight percent) sodium and potassium oxides are roughly equivalent in performance, based on benzene yields and low hexane by-product formation and rubidium is less effective. When the rubidium concentration is doubled to about eight weight percent, Run 12, production of benzene is doubled, while at the same promoter level, Run 6, shows that sodium is less effective than rubidium.

Thus, it is seen that for a given alkali metal, the optimum performance expected depends to some extent upon the atomic weight of alkali metal chosen. Runs 13–14 demonstrate that the alkali metal compound used to impregnate the alumina should not be chosen from among the halides and sulfates since inactive catalysts will result when such salts are employed. The curve in FIG. 1 clearly shows the interrelationship between benzene production and added sodium promoter.

EXAMPLE II

A series of catalysts was prepared by impregnating individual samples of 20–40 mesh particles of a commercially available alumina having a surface area of about 240 m$^2$/g with an aqueous solution of sodium hydroxide sufficient to impart various amounts of sodium to each support. Each composite was dried, calcined, charged to a reactor and tested for dehydrocyclization of hexene-1 at a pressure of one atmosphere (absolute) in a 30-minute run. Test conditions employed included a hydrocarbon feed rate of about 0.5 LHSV and a reactor temperature of about 1000° F. (538° C.). The total product composition of each effluent was determined as before by GLC. The results obtained are presented in graphical form in FIG. 2.

Figure 2:
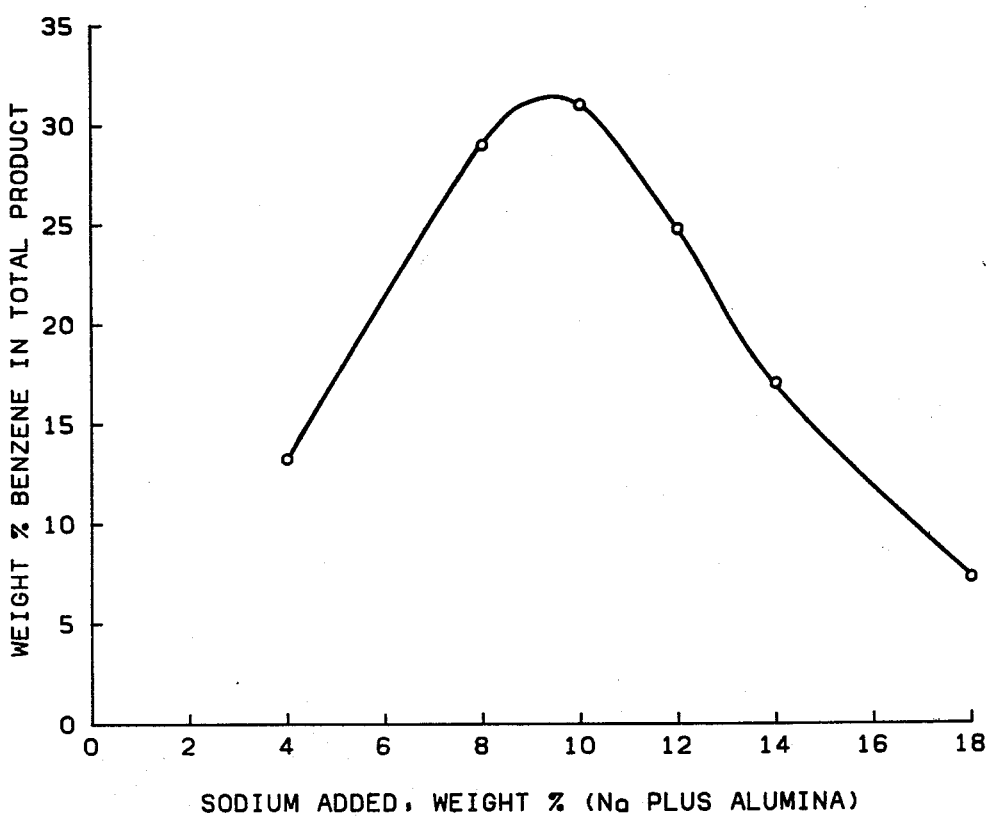

Inspection of FIG. 2 shows that benzene yields are superior for catalysts obtained by promoting an alumina having a surface area of about 240 m$^2$/g with from about 5–14 weight percent of added sodium and especially from about 7–12 weight percent.

EXAMPLE III

A series of catalysts was prepared by impregnating individual samples of commercially available aluminas having different surface areas with aqueous solutions of sodium hydroxide sufficient to impart various amounts of sodium for each catalyst composite. A catalytic grade silica was also impregnated with aqueous sodium hydroxide. Each sample of alumina and the silica was in the form of 20–40 mesh particles. Each composite was dried, calcined, charged to a reactor, and tested for dehydrocyclization of hexene-1 at a pressure of one atmosphere (absolute) as described in Example I. Reactor effluents were treated and identified in the manner described in Example I. The promoter concentrations employed with alumina samples having different surface areas, reactor conditions used, and results obtained are presented in Table II.

TABLE II

Dehydrocyclization of Hexene-1 over Sodium Oxide-Promoted Catalysts

| Run No. | 4[1] | 6[1] | 15 | 16 | 17 | 18 | 19 |
|---|---|---|---|---|---|---|---|
| Sodium, Wt. % | 3.9 | 7.9 | 4.0 | 7.9 | 4.0 | 8.0 | 4.2 |
| Surface Area: | | | | | | | |
| Alumina, m$^2$/g | 91 | 91 | 240 | 240 | 338 | 338 | — |
| Silica, m$^2$/g | — | — | — | — | — | — | 88 |
| Test Conditions: | | | | | | | |
| Temp. °F. | 1009 | 1001 | 1004 | 1003 | 1004 | 999 | 1006 |
| Temp., °C. | 543 | 538 | 540 | 539 | 540 | 537 | 541 |
| LHSV | 0.4 | 0.5 | 0.6 | 0.6 | 0.45 | 0.5 | 0.6 |
| Sample Period, hrs. | 1.2–1.7 | 0.9–1.6 | 0.7–1.0 | 0.7–1.0 | 0.7–1.0 | 0.7–1.2 | 0.7–1.0 |

TABLE II-continued

Dehydrocyclization of Hexene-1 over Sodium Oxide-Promoted Catalysts

| Run No. | 4[1] | 6[1] | 15 | 16 | 17 | 18 | 19 |
|---|---|---|---|---|---|---|---|
| Benzene, Wt. % | 49.9 | 30.4 | 15.8 | 44.5 | 3.2 | 36.0 | none detected |
| n-Hexane, Wt. % | 6 | 9 | 3 | 3 | 3 | 4 | nd[2] |
| Remarks | Invention | Invention | Control | Invention | Control | Invention | Control |

[1] Repeated from Table I.
[2] Not determined.

The lack of benzene produced in control Run 19 demonstrates that silica is not equivalent to alumina in forming an active alkali metal oxide-promoted catalyst for dehydrocyclization. The results for Runs 4, 6, and 15-18 show that best benzene yields depend upon both the sodium promoter concentration and the surface area of the alumina. Runs 4 and 6 show that for an alumina having a surface area of about 91 m²/g a sodium promoter concentration of about four weight percent gives good results whereas for a sodium promoter level of about eight percent a less active catalyst results. Runs 15-18 show that when aluminas having surface areas of about 240 and 338 m²/g are used, a sodium promoter concentration of four weight percent is not sufficient to provide adequate production of benzene from hexene-1. When the sodium promoter concentration is increased to eight weight percent, however, active catalysts are formed as the results of Runs 16 and 18 indicate. The data suggest that a sodium promoter concentration of greater than eight weight percent, for the alumina having a surface area of about 338 m²/g, might give a catalyst having more dehydrocyclization activity than the catalyst used in Run 18.

EXAMPLE IV

A series of catalysts was prepared by impregnating individual samples of 20-40 mesh particles of the aluminas used in preparing Example II catalysts with both sodium and chromium oxides. The sodium was added first by impregnating each alumina sample with aqueous sodium hydroxide solution, drying the mixture at 240° F. and calcining the product at 900° F. for two hours. Each cooled, sodium-containing sample was then impregnated with an aqueous solution of chromium nitrate or chromium trioxide, dried at 240° F. and calcined two hours at 900° F. Each catalyst sample was tested for dehydrocyclization of hexene-1 at a pressure of one atmosphere (absolute) as in the previous Examples. Reactor effluents were treated and their components determined as before. The promoter concentrations employed with alumina samples having different surface areas, the chromium compound used, the reactor conditions employed, and results obtained are presented in Table III.

TABLE III

Dehydrocyclization of Hexene-1 over Sodium Oxide/Chromia/Alumina Catalysts

| Run No. | Alumina, Surface Area, m²/g | Sodium Added Wt.% | Chromium Added Wt.% | Initial Chromium Compound | Na/Cr, Weight Ratio | Temperature °F. | Temperature °C. | LHSV | Sample Period, Hours | Benzene,[a] Wt. % | n-Hexane,[b] Wt. % | Remarks |
|---|---|---|---|---|---|---|---|---|---|---|---|---|
| 20 | 91 | 2.0 | 2.0 | CrNO₃ | 1 | 1003 | 539 | 0.5 | 0.7-1.0 | 86.4 | 82 | Control |
| 21 | 91 | 1.9 | 5.0 | ↓ | 0.4 | 1004 | 540 | 0.5 | 0.7-1.0 | 91.2 | 87 | Control |
| 22 | 91 | 3.9 | 2.0 | ↓ | 2.0 | 1001 | 538 | 0.45 | 0.7-1.0 | 50.7 | 9 | Invention |
| 23 | 91 | 3.8 | 5.0 | ↓ | 0.8 | 997 | 536 | 0.6 | 0.7-1.0 | 75.5 | 26 | Invention |
| 24 | 91 | 3.6 | 10.0 | CrO₃ | 0.4 | 1003 | 539 | 0.6 | 0.7-1.1 | 88.8 | 83 | Control |
| 25 | 91 | 7.1 | 10.0 | ↓ | 0.7 | 1004 | 540 | 0.45 | 0.7-1.0 | 71.3 | 16 | Invention |
| 26 | 91 | 18.0 | 10.0 | ↓ | 1.8 | 1001 | 538 | 0.45 | 0.7-1.0 | 19.8 | 4 | Control |
| 27 | 240 | 4.8 | 5.0 | ↓ | 1.0 | 1003 | 539 | 0.5 | 0.7-1.0 | 89.9 | 83 | Control |
| 28 | 240 | 7.5 | 5.0 | ↓ | 1.5 | 1003 | 539 | 0.6 | 0.7-1.0 | 66.6 | 18 | Invention |
| 29 | 240 | 7.1 | 10.0 | ↓ | 0.7 | 1001 | 538 | 0.6 | 0.7-1.0 | 89.2 | 83 | Control |
| 30 | 240 | 11.7 | 10.0 | ↓ | 1.2 | 1004 | 540 | 0.5 | 0.7-1.0 | 69.2 | 16 | Invention |
| 31 | 338 | 3.8 | 5.0 | CrNO₃ | 0.8 | 1001 | 538 | 0.5 | 0.7-1.2 | 89.2 | 65 | Control |
| 32 | 338 | 7.6 | 5.0 | ↓ | 1.5 | 1004 | 540 | 0.5 | 0.7-1.2 | 51.4 | 8 | Invention |
| 33 | 7.4 | 7.0 | | CrO₃ | 1.1 | 1005 | 541 | 0.5 | 0.7-1.0 | 82.2 | 53 | Control |
| 34 | 338 | 10.9 | 9.0 | ↓ | 1.2 | 1005 | 541 | 0.6 | 0.7-1.0 | 55.2 | 11 | Invention |

[a] Benzene content of liquid product collected in wet ice-cooled trap.
[b] See page 7, lines 19-22, for determination of n-hexane.

Inspection of Table III results indicates that very active dehydrocyclization catalysts are made by promoting aluminas with both sodium and chromium oxides. To maintain such activity while simultaneously suppressing hydrogenation activity requires a fairly narrow range of sodium and chromium concentrations, as well as a narrow sodium/chromium weight ratio range, as set forth in Table B. Metal concentrations and weight ratios in turn are dependent upon the surface area of the aluminas to obtain the desired catalysts. With catalysts based on alumina having a surface area of 91 m²/g, control Runs 20 and 21 show that the sodium contents are too low (less than the desirable 3-12 weight percent) even though the Na/Cr weight ratios are in or close to the desirable 0.5-2.2 range. As a result, high dehydrocyclization activity to benzene results, as well as high hydrogenation activity of hexene-1 feed to n-hexane. Control Run 24 results are similar to Runs 20 and 21. Although the sodium content of 3.6 weight percent is in the desired range, the Na/Cr weight ratio is less than the 0.5 minimum specified. As a result, high dehydrocyclization activity and high hydrogenation activity are evident. Control Run 26 shows that low hydrogenation activity and low dehydrocyclization activity result when the sodium content (18 weight percent) is above the specified 12 weight percent, even though the Na/Cr weight ratio of 1.8 is within the desirable 0.5-2.2 range. Invention Runs 22, 23, and 25 demonstrate that high dehydrocyclization activity and low hydrogenation activity result when the sodium contents and Na/Cr weight ratios are within the stated ranges.

With alumina of 240 m²/g, or 338 m²/g, control Runs 27, 29, 31, and 33 demonstrate that the sodium contents must be within 6–18 weight percent and Na/Cr ratios of 1.2–1.8 must be maintained otherwise high dehydrocyclization activity and high hydrogenation activity result. When proper ranges are observed, the aforementioned desirable results are obtained as invention Runs 28, 30, 32, and 34 demonstrate.

EXAMPLE V

A series of catalysts was prepared by impregnating individual samples of 20–40 mesh particles of the alumina having a surface area of 91 m²/g with an aqueous solution of an alkali metal salt, drying each mixture at 240° F. and calcining the products for two hours at 900° F. Each recovered composite was then impregnated with an aqueous solution of chromium nitrate, dried at 240° F., and calcined two hours at 900° F. Each catalyst sample was tested for dehydrocyclization of hexene-1 or heptene-1 at a pressure of one atmosphere (absolute) as in the previous Examples. Reactor effluents were treated and their components determined as before. The alkali metal promoters used and concentrations thereof, as well as concentrations of the chromium promoter, reactor conditions employed, and results obtained, are presented in Table IV.

Runs 23 (repeated from Table III), 41, and 42, each catalyst containing the same amount of sodium and chromium promoter, demonstrate that the sodium component is preferably derived from sodium hydroxide (Run 23) for best results. Unlike the alkali metal-promoted aluminas, however, sodium sulfate can be employed to obtain a catalyst having less activity (Run 41) than that of Run 23, but still satisfactory. The poor results shown in Run 42 indicate that sodium chloride is not a satisfactory replacement for sodium hydroxide as a source of the sodium promoter in the invention catalysts. In Table IV, the weight percent values for benzene and n-hexane are determined in the manner set forth in footnotes (a) and (b) of Table III.

I claim:

1. A process for the conversion of nonaromatic hydrocarbons to aromatic hydrocarbons which comprises contacting a hydrocarbon-containing feedstock comprising aliphatic hydrocarbons under dehydrocyclization conditions of temperature and pressure with a catalyst consisting of alumina having a surface area of at least 50 m²/g promoted with an alkali metal oxide selected from the group consisting of the oxides of sodium, potassium, rubidium, and cesium wherein the catalyst contains (1) about 2–14 weight percent of sodium or potassium or (2) about 3–18 weight percent of rubidium or cesium.

2. A process according to claim 1 wherein the feed-

TABLE IV

| | Monoolefin Dehydrocyclization over Alkali Metal Oxide/Chromia/Alumina Catalysts | | | | | | | | | | | | | |
|---|---|---|---|---|---|---|---|---|---|---|---|---|---|---|
| | Alumina | | Chromium | Alkali | | Test Conditions | | | | Weight Percent | | | | |
| Run No. | Surface Area, m²/g | Alkali Metal Added - Wt.% | Added Wt. % | Metal/Cr, Wt. Ratio | Monoolefin Feed | Temp., °F. | °C. | LHSV | Sample Period, Hours | Benzene | Toluene | n-Hexand | n-Heptane | Remarks |
| 35 | 91 | K | 3.3 | 2.5 | 1.3 | Hexene-1 | 1002 | 539 | 0.54 | 0.7–1.0 | 90.2 | nd[4] | 87 | nd | Control |
| 36 | 91 | K | 3.2 | 5.0 | 0.6 | Hexene-1 | 999 | 537 | 0.45 | 0.7–1.0 | 90.5 | nd | 87 | nd | Control |
| 37 | 91 | K | 6.5 | 5.0 | 1.3 | Hexene-1 | 1003 | 539 | 0.63 | 0.7–1.0 | 54.3 | nd | 4 | nd | Invention |
| 38 | 91 | K | 6.3 | 7.5 | 0.8 | Hexene-1 | 1003 | 539 | 0.53 | 0.7–1.0 | 83.9 | nd | 23 | nd | Invention |
| 39 | 91 | K | 3.3 | 5.0 | 0.7 | Heptene-1 | 899 | 482 | 0.60 | 0–0.3 | 3.3 | 61.2 | nd | 82 | Control |
| 40 | 91 | Na | 3.8 | 5.0 | 0.8 | Heptene-1 | 902 | 483 | 0.45 | 0–0.3 | 2.1 | 58.6 | nd | 41 | Invention |
| 23[1] | 91 | Na | 3.8 | 5.0 | 0.8 | Hexene-1 | 997 | 536 | 0.60 | 0.7–1.0 | 75.5 | nd | 26 | nd | Invention |
| 41 | 91 | Na[2] | 3.8 | 5.0 | 0.8 | Hexene-1 | 1005 | 541 | 0.50 | 0.7–1.0 | 53.9 | nd | 15 | nd | Invention |
| 42 | 91 | Na[3] | 3.8 | 5.0 | 0.8 | Hexene-1 | 1003 | 539 | 0.50 | 0.7–1.0 | 20.6 | nd | 5 | nd | Control |

[1] Repeated from Table III.
[2] Used aqueous Na₂SO₄ to impregnate support.
[3] Used aqueous NaCl to impregnate support.
[4] nd, where used, indicates not determined.

Inspection of Table IV results show for control Runs 35 and 36 with catalysts containing potassium and chromium promoters that high dehydrocyclization activity for conversion of hexene-1 feed to benzene was achieved. When the potassium concentration was within the invention specified 5–16 weight percent and K/Cr weight ratio 0.7–1.5, invention Runs 37 and 38 show that the catalysts having both high dehydrocyclization activity for conversion of hexene-1 coupled with low hydrogenation activity are obtained.

Heptene-1 was passed over a K/Cr-promoted catalyst in control Run 39 and a Na/Cr-promoted catalyst in invention Run 40. The potassium level of 3.3 weight percent in Run 39 was below the specified minimum level of five weight percent, thus a catalyst was obtained that also possessed a relatively high hydrogenation activity even though the K/Cr weight ratio was in the specified range of 0.7–1.5. Invention catalyst, Run 40, contained the specified amount of each promoter, hence the results show that high conversion of heptene-1 feed to toluene was achieved whereas low hydrogenation of heptene-1 to n-heptane was observed.

stock comprises olefins having from 6 to 12 carbon atoms per molecule and the dehydrocyclization conditions include a temperature of about 700°–1100° F. (371°–593° C.).

3. A process according to claim 1 wherein the feedstock is a mixture of hydrocarbons boiling in the gasoline range of about 100°–425° F. (38°–218° C.) relatively free of aromatic hydrocarbons and the dehydrocyclization conditions include a temperature of about 700°–1100° F. (371°–593° C.).

4. A process according to claim 1 wherein the catalyst is (1) alumina having a surface area in the range of 50–150 m²/g and a sodium or potassium content of 2–8 weight percent or (2) alumina having a surface area of 150–350 m²/g and a sodium or potassium content of 5–14 weight percent, and the dehydrocyclization conditions include a temperature ranging from about 700°–1100° F. (371°–593° C.).

5. A process according to claim 1 wherein the catalyst is (1) alumina having a surface area of 50–150 m²/g and a rubidium or cesium content of 3–12 weight percent or (2) alumina having a surface area of 150–350

$m^2/g$ and a rubidium or cesium content of 6–18 weight percent, and the dehydrocyclization conditions include a temperature in the range of about 700°–1100° F. (371°–593° C.).

6. A process for the conversion of nonaromatic hydrocarbons to aromatic hydrocarbons which comprises contacting a hydrocarbon-containing feedstock comprising aliphatic hydrocarbons under dehydrocyclization conditions of temperature and pressure with a catalyst having high dehydrocyclization activity and low hydrogenation activity consisting of chromium, sodium and alumina wherein the catalyst contains (1) from 1.4 to 24 weight percent chromium when the alumina has a surface area of 50–150 $m^2/g$ and sodium in an amount of 3–12 weight percent with a sodium/chromium weight ratio of 0.5–2.2 or (2) from 3.3 to 15 weight percent chromium when the alumina has a surface area of 150–350 $m^2/g$ and sodium in an amount of 6–18 weight percent with a sodium/chromium weight ratio of 1.2–1.8, and the dehydrocyclization conditions include a temperature of about 700°–1100° F. (371°–593° C.).

7. A process for the conversion of nonaromatic hydrocarbons to aromatic hydrocarbons which comprises contacting a hydrocarbon-containing feedstock comprising aliphatic hydrocarbons under dehydrocyclization conditions of temperature and pressure with a catalyst having high dehydrocyclization activity and low hydrogenation activity consisting of chromium, potassium and alumina wherein the catalyst contains (1) from 3.3 to 22.9 weight percent chromium when the alumina has a surface area of 50–150 $m^2/g$ and potassium in an amount of 5–16 weight percent with a potassium/chromium weight ratio of 0.7–1.5 or (2) from 5.3–28.6 weight percent chromium when the alumina has a surface area of 150–350 $m^2/g$ and potassium in an amount of 8–20 weight percent with a potassium/chromium weight ratio of 0.7–1.5, and the dehydrocyclization conditions include a temperature of about 700°–1100° F. (371°–593° C.).

8. A process according to claim 1 wherein the dehydrocyclization conditions include a temperature ranging from about 700°–1100° F. (371°–593° C.), a pressure ranging from about 0 to 300 psig (0–2068 kPa gage), a hydrogen/hydrocarbon mole ratio of about 0.5 and hydrocarbon feedstock is passed through the reaction zone at a liquid hourly space velocity (LHSV) ranging from about 0.2–5 volumes of hydrocarbon feed per volume of catalyst per hour.

9. A process according to claim 2 wherein the feedstock comprises hexene-1 or heptene-1 and the dehydrocyclization conditions include a temperature of about 700°–1100° F. (371°–593° C.).

* * * * *